United States Patent [19]
Benetti

[11] Patent Number: 5,203,450
[45] Date of Patent: Apr. 20, 1993

[54] COMBINATION DISPLAY AND PACKAGING CONTAINER FOR DENTAL MATERIAL

[75] Inventor: Vincent M. Benetti, Vacaville, Calif.

[73] Assignee: Aalba Dent, Inc., Cordelia, Calif.

[21] Appl. No.: 834,485

[22] Filed: Feb. 12, 1992

[51] Int. Cl.$^5$ .............................................. B65D 85/00
[52] U.S. Cl. ................................. 206/63.5; 206/564; 206/565
[58] Field of Search ............. 206/0.8, 0.81–0.84, 206/368, 369, 370, 564, 560, 565, 570, 63.5

[56] References Cited

U.S. PATENT DOCUMENTS

| | | | |
|---|---|---|---|
| 376,889 | 1/1888 | Kearsing. | |
| 3,013,656 | 12/1961 | Murphy, Jr. | 206/564 |
| 3,057,459 | 10/1962 | Burdick | 206/0.83 |
| 4,046,254 | 9/1977 | Kramer | 206/370 |
| 4,898,276 | 2/1990 | Georgakis | 206/369 |
| 5,033,774 | 7/1991 | Benardelli | 206/0.83 |
| 5,119,940 | 6/1992 | Grindrod | 206/564 |

Primary Examiner—Jimmy G. Foster
Attorney, Agent, or Firm—John P. Sutton

[57] ABSTRACT

A system for ingots of holding dental material includes a holder having a plurality of spaced-apart depressions each configured to hold one ingot. The container has a retaining cover for retaining the holder and ingots in the container. The container also has a master cover which when closed encloses a storage space between it and the retaining cover. The container and covers may be made from a transparent material such that ingots in the container are visible even when the container is closed.

6 Claims, 4 Drawing Sheets

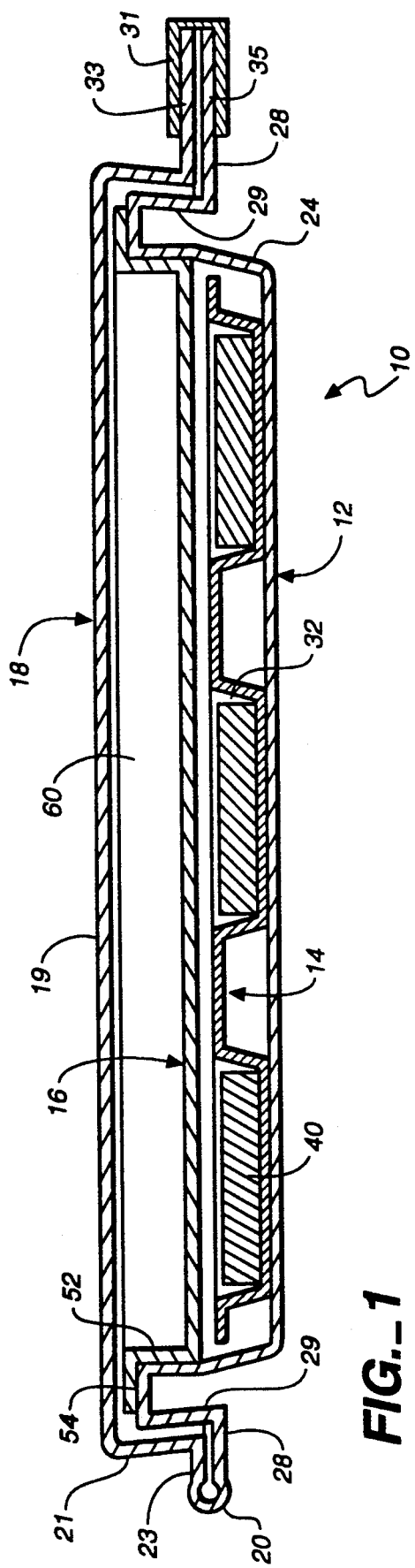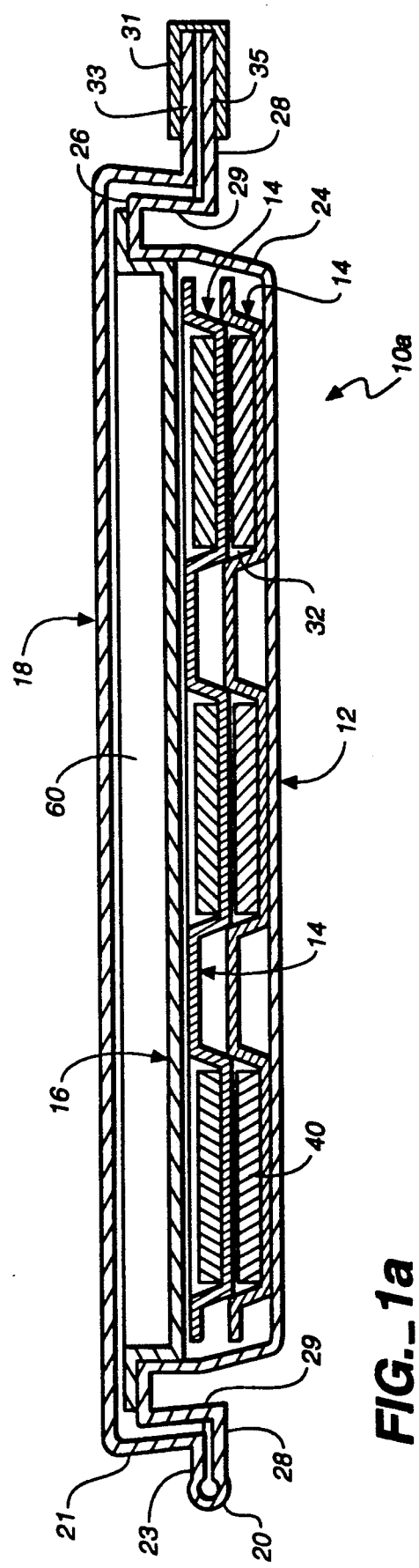

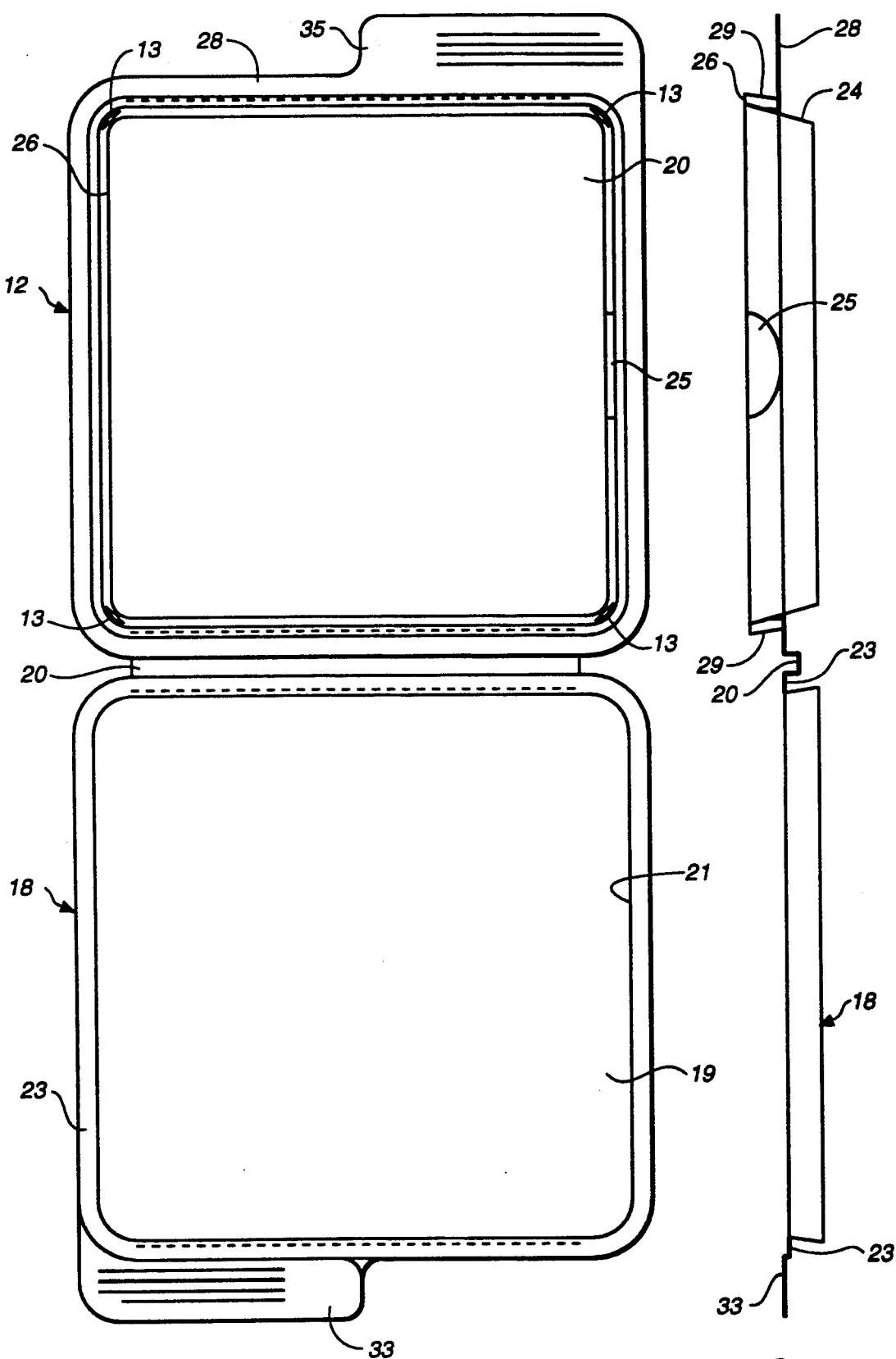
FIG._2  FIG._3

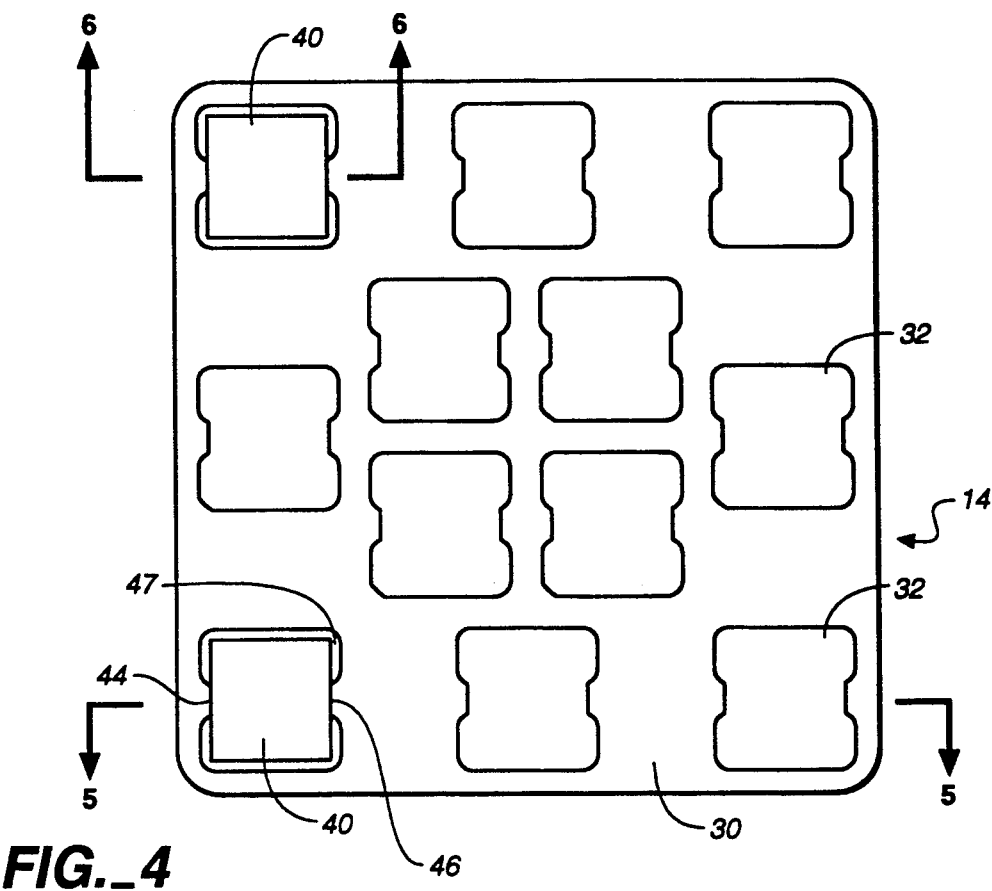
FIG._4
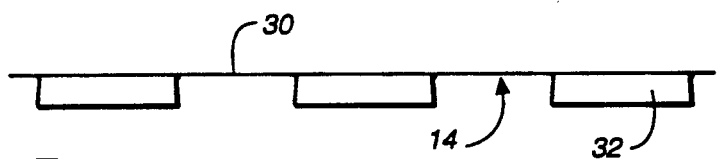
FIG._5
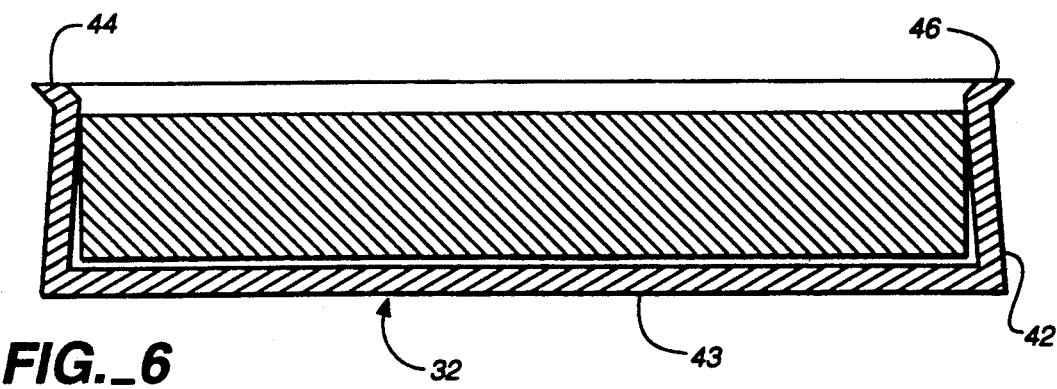
FIG._6

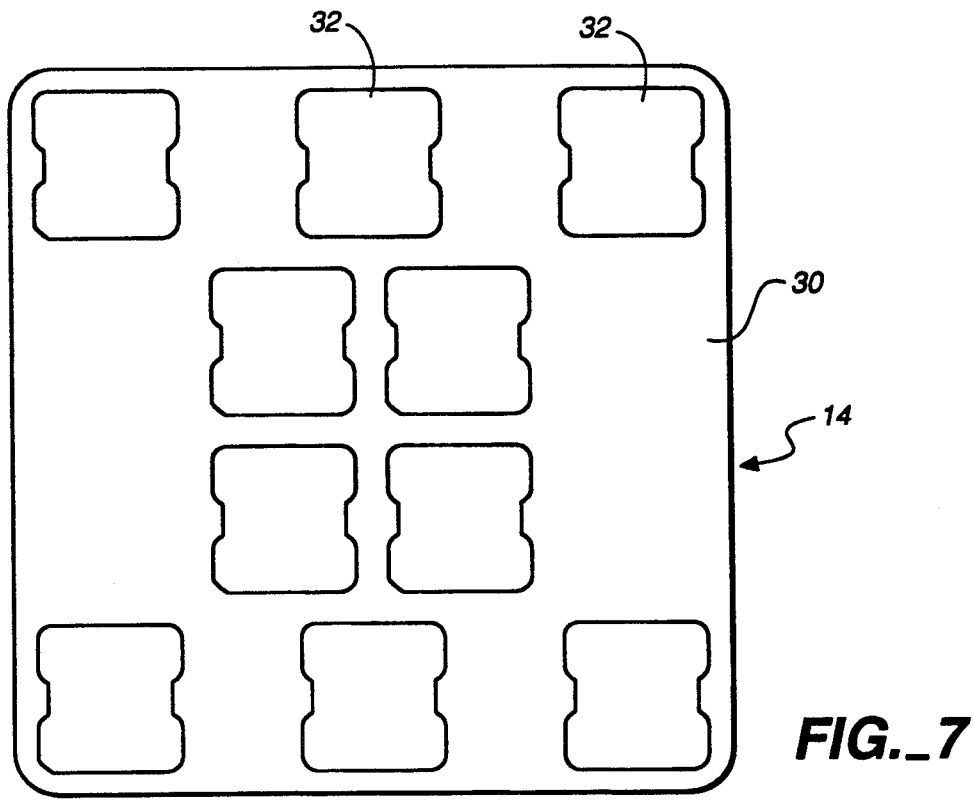
FIG._7
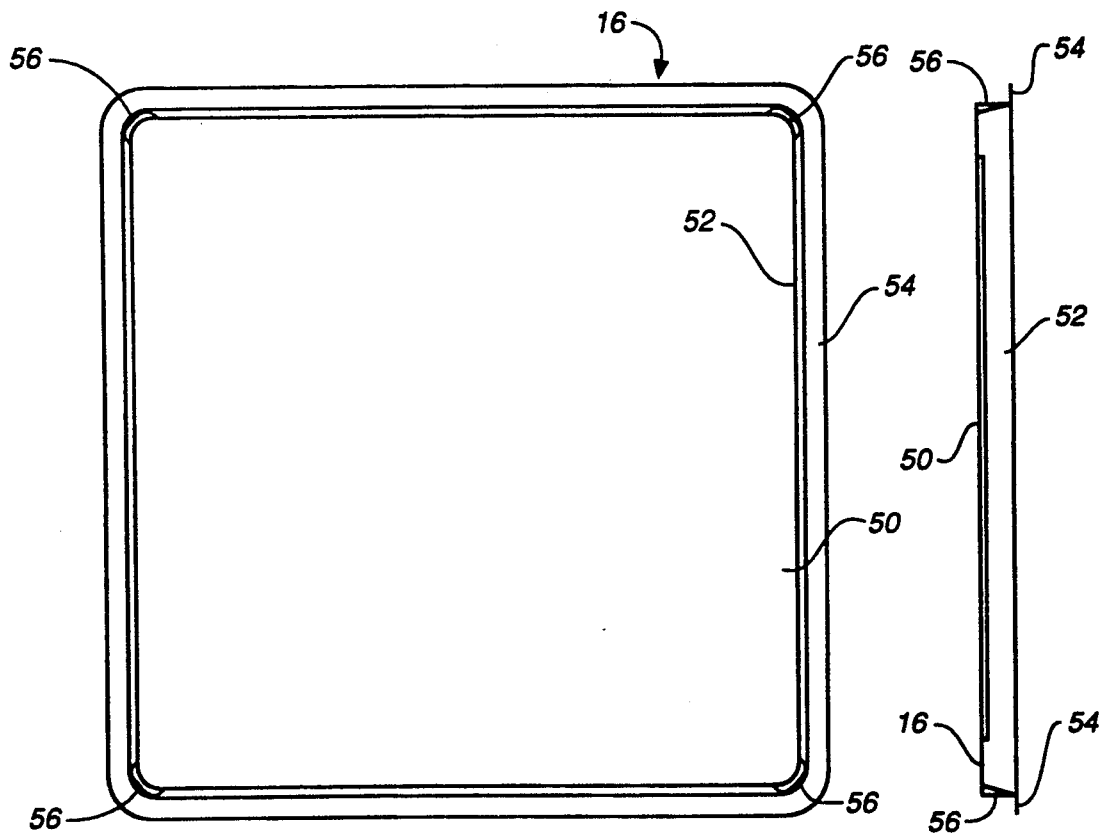
FIG._8  FIG._9

COMBINATION DISPLAY AND PACKAGING CONTAINER FOR DENTAL MATERIAL

BACKGROUND OF THE INVENTION

The present invention relates in general to containers for storing and transporting dental materials. It relates in particular to a container for holding and displaying ingots of precious metal, nonprecious metal, and metal alloy dental material.

Metals used in dental repair and reconstruction, for example, for making crowns and bridges, include precious metals such as gold and less precious alloys formulated to provide desirable properties of precious metals at less cost. Such reconstruction metals are generally delivered to a laboratory in the form of ingots. Dental reconstruction metals are sold in units of troy ounces. The weight of ingots is usually either one or two pennyweights.

Such metal and metal alloy dental materials are valuable products which may be scarce and expensive, thus it is generally economically preferable for a laboratory to maintain a minimum inventory of material. It is desirable, however, that an inventory position be readily and rapidly assessable to avoid material shortages. Preferably, the material should be readily accessible for use and for inventory check. It is desirable however that this inventory check be made without a requirement to count ingots stored loosely, and without the risk of spilling and mislaying loose ingots as they are counted.

Ingots of metal or metal alloy may carry a mark or logo which identifies, for example, the origin, weight, or type of the metal or alloy. This enables, for example, alloys to be distinguished one from another, and distinguished from precious metals of similar appearance. Preferably, a container for shipping and transporting such materials should allow logos on each ingot in the container to be quickly and positively identified. A container should also be designed such that it may be moved without the risk of ingots abrading against each other or being abraded by foreign objects. Such abrasion may remove a logo from an ingot making it difficult to identify.

Accordingly, it is an object of the present invention to provide a system for holding ingots of metal or alloy dental material.

It is another object of the invention to provide a system for holding ingots separately and securely.

It is a further object of the invention to provide a container for holding ingots wherein all ingots therein may be visible without opening the container and without removing them from the container.

SUMMARY OF THE INVENTION

The present invention is directed to a system for holding metal or metal alloy dental material in the form of ingots.

The system includes a container including a generally flat holding member for holding the ingots. The holding member includes a plurality of spaced-apart depressions. Each of the depressions is configured to hold one ingot.

Secured to the container is a first cover for retaining the holding member in the container. A second cover may be secured to the container over the first cover. The first cover and the second cover may be arranged such that a space is enclosed between them. The storage space may be used as a storage for storing printed material such as instructions for use of the ingots.

In a preferred embodiment, the container, the holding member, and the first and second covers are made from a flexible transparent plastic material. As such, ingots in the container may be visible when the container is closed. The container, and the first and second covers may be configured such that the first and second covers may be secured to the container by a press fit.

BRIEF DESCRIPTION OF THE DRAWING

The accompanying drawings, which are incorporated in and constitute a part of the specification, schematically illustrate a preferred embodiment of the present invention, and together with the general description given above and the detailed description of the preferred embodiment given below, serve to explain the principles of the invention.

FIG. 1 is a cross-sectional view schematically illustrating one embodiment of a system according to the present invention.

FIG. 1a is a cross-sectional view schematically illustrating an alternate arrangement the system of FIG. 1.

FIG. 2 schematically illustrates a plan view of a container and hinged cover for of system of FIG. 1.

FIG. 3 is a side elevation schematically illustrating the container and hinged cover of FIG. 2.

FIG. 4 schematically illustrates a plan view of an ingot holding member for the system of FIG. 1.

FIG. 5 is a cross section in the direction of line 5—5 of FIG. 4 illustrating depressions for holding ingots.

FIG. 6 is a cross section in the direction of line 6—6 of FIG. 4 showing details of a depression for holding an ingot.

FIG. 7 shows an alternate arrangement of depressions for the ingot holding member of FIG. 4.

FIG. 8 is a plan view schematically illustrating retaining cover for the system of FIG. 1.

FIG. 9 schematically illustrates a side elevation view of the retaining cover of FIG. 8.

DETAILED DESCRIPTION OF THE INVENTION

Turning now to the drawings wherein like components are designated by like reference numerals, FIG. 1 shows one embodiment of a system for holding ingots of dental material. The system is designated generally by the numeral 10. Principle components of the system include a container 12, an ingot holding member 14, a first cover 16, which may be referred to as a retaining cover, and a second cover 18 which may be referred to as a master cover. Master cover 18 may be attached to container 12 by a hinge member 20.

Preferably, principle components of the system are made from a flexible transparent plastic material for reasons which will be explained throughout the detailed description of the system set forth below. One reason for selecting a flexible transparent plastic material, for example, for principle components is that they may be inexpensively produced by well-known injection molding or thermoforming processes. Further, container 12, master cover 18, and hinge member 20 may be molded as a single unit as shown in FIG. 2.

Container 12 includes a base 22, and a wall 24. Container 12 has an open top which is surrounded by a rim 26. The rim has an outwardly extending flange 28, which may be referred to as the container flange, extending therefrom.

Referring now to FIGS. 4, 5, and 6, ingot holding member 14 comprises a generally flat sheet 30 having a plurality of spaced-apart depressions 32 therein. Holding member 14 may be characterized as a removable base for container 12. A depression 32 includes a wall 42 and a base 43. Each depression 32 is configured to hold one ingot or unit of shaped product. As such the ingots are held in noncontiguous spaced-apart relationship in holding member 14. Depression 32 is preferably about ten percent deeper than the thickest ingot to be stored therein. An ingot surface may thus be protected from abrasion, for example, by an object inadvertently placed on holding member 14, or when one or more holding members are stacked together. For the purposes of this description ingots are assumed to be rectangular, which is a common shape for ingots of dental material. It will be evident, however, that ingots or other valuable shaped objects may have some other shape, for example, square, triangular, hexagonal, round or elliptical, for convenience or aesthetic reasons. The number of depressions 32, i.e., ingots held, by a holding member may be determined, for example, by shipping quantity, usage rate, ingot size, or simply aesthetic reasons. For reasons of aesthetics or convenience ingots 32 may be arranged in a regular or symmetrical pattern as illustrated in FIGS. 4 and 7 wherein twelve and ten depressions, respectively, per holding member 14 are depicted.

For thinner ingots, two or more holding members 14 may be stacked within container 12 as shown in FIG. 1a (System 10a). Resilient protective packing material (not shown) may be placed between holding members 14 or between a holding member 14 and retaining cover 16, for example, to prevent excess motion of the holding members during transport.

Turning again to FIGS. 4 and 6, a means of securing an ingot 40 in a depression 32 is described. Here, a wall 42 of depression 32 is sloped inwardly at two or more portions 44 and 46, forming detents preferably on opposite edges of depression 32. Wall portions 44 and 46 are arranged such that the distance therebetween is slightly less than the corresponding dimension of an ingot to be placed in the depression. An ingot may be pressed into the depression causing wall portions 44 and 46 to deform and thus allow its entry into the depression. Wall portions 44 and 46 may then return partially or completely to their original shape, securing or frictionally gripping ingot 40 at opposite edges in depression 32. An ingot 40, thus secured in a depression 32, may be referred to as secured therein by a press fit. A depression 32 is preferably arranged such that a clearance space 47 is provided between the ingot and wall 42 of the depression. As such, an ingot may be readily removed from a depression, for example, by tweezers, a lever, or simply by pressing manually on base 43 of the depression.

Retaining cover 16 provides a means for retaining holding member 14 in container 12 and means for keeping foreign objects from contacting ingots or shaped products in holding member 14. Retaining cover 16 also provides additional means for retaining ingots 40 in holder 14 should they become dislodged from depressions 32. Ingots may become dislodged, for example, by a shock due to dropping the container. Ingots may also become loose in the holder in the event of a permanent deformation of wall portions 44 and 46, or may simply fit loosely due to an under tolerance dimension.

Referring now to FIGS. 8 and 9, one form of a retaining cover 16 is shown. The cover has a generally flat base 50 and an upwardly extending wall 52 surrounded by a narrow outwardly extending seating flange 54. Seating flange 54 is preferably no wider than rim 26 of container 12. In corners 56 of retaining cover 16, wall 52 is extended outward at the base such that it slopes inward as it extends upward from base 50. It may be sloped, for example, at about five degrees from the perpendicular direction.

Referring again to FIG. 2, in corners 13 of container 12, wall 24 also slopes inward, for example, at about five degrees as it extends upwards away from base 22. Retaining cover 16 may be press fit into container 12 such that wall 52, at corners 56, fits under wall 24 at corners 13 of container 12. As such, cover 16 may be secured in container 12 by a press fit. Seating flange 54 seats on rim 26 of container 12 such that cover 16 overlays base 30 at a distance from it such that it does not contact or abrade ingots or shaped products in depressions 32. Referring to FIG. 3, a notch 25 may be provided in rim 26 and wall 24 such that retaining cover 16 may be prized out of container 12, for example, by urging it upward with a finger or a lever.

Master cover 18 has a top 19 and a downward extending wall 21 sloping inwardly as it extends downward, for example, at about five degrees from perpendicular. Wall 21 is surrounded by a flange 23. When master cover 18 is pressed over rim 26 (see FIG. 1), a downward extending portion 29 of rim 26 is caused to flex inward. Wall 21 thus, effectively, fits under rim 26 and secures master cover 18 to container 12. Thus, master cover 18 is secured over container 12 and retaining cover 16 by a press fit. Master cover 18 may be additionally secured to container 12 by attaching a tab 33 (extending from flange 23 of cover 18) and a tab 35 (extending from flange 28 of container 12). Tabs 33 and 35 may be attached, for example, by a strip of adhesive tape 31. Cover 18 may be opened by pulling apart tabs 33 and 35.

When master cover 18 is secured over retaining cover 16, a space 60 therebetween is enclosed. Space 60 may be used for storing printed matter such as instructional literature or product data sheets. As such, master cover 18 may be opened, and matter in space 60 removed, without disturbing ingots held in holding member 14 in container 12.

As discussed above, metal or metal alloy dental material is commonly supplied to a user in the form of ingots. The ingots are usually cut or stamped from rolled sheet stock. The ingots may have a thickness between about 0.025 centimeters (cm) and 0.5 cm, a length between about 1.0 cm and 2.2 cm, and a width between about 0.5 cm and 2.2 cm. As depression 32 may have overall dimensions up to about ten percent greater that the largest ingot to be held therein, to provide, for example, clearance space 47. As such, a depression may have a depth between about 0.025 centimeters (cm) and 0.55 cm, a length between about 1.0 cm and 2.4 cm, and a width between about 0.5 cm and 2.4 cm. A holding member may be configured to hold from one to sixty ingots. A holding member is configured to be interchangeable within a particular container size. As such, one size of container may be used to ship different quantities and weights.

A container may be manufactured in different sizes for accommodating different shipping quantities of ingots. A container may have a depth between about 0.6 cm and 2.0 cm, a length between about 7.6 cm and 17.8 cm, and a width between about 2.5 cm and 12.7 cm.

A system for holding ingots of metal or metal alloy dental material has been described. The system includes a holding member having spaced-apart depressions for holding ingots securely and separately. The holding member is placed inside a container. A retaining cover is secured in the container and prevents the retaining member from falling out of the container as well as providing additional means to retain ingots in the holding member. Ingots are thus prevented from abrading against each other when the system is moved or transported.

The container is provided with a master cover, which when secured on the container, encloses a space between it and the retaining cover. The space may be used, for example, as storage space for storing printed matter. Printed matter stored in the space may thus be removed without disturbing ingots stored in the container.

Principle components of the system may be constructed from a flexible transparent plastic material. As such, depressions in the holding member may be configured to hold ingots securely by a press fit, and covers may be configured to be secured on or in the container by a press fit. Transparent plastic material allows ingots in the container to be visible, even when the container is closed by one or both of the covers. Ingots may thus be counted or identified without opening the container.

The present invention has been described in terms of a preferred and other embodiments. The invention is not limited, however by the embodiments described or depicted. Rather, the invention is limited by the appended claims.

What is claimed is:

1. A system for holding ingots of dental material, comprising:
   a container having an open top including a rim;
   within said container at least one generally flat holding member having a plurality of spaced-apart depressions therein each of said depressions configured to contain one ingot, and each of said depressions including means for retaining said ingot therein;
   a first cover secured in said container below said rim portion for retaining said holding member in said container; and
   a second cover secured on said container over said first cover and forming a storage space between said first and second covers.

2. The system of claim 1 wherein said container and said first and second covers are formed from a flexible transparent plastic material.

3. The system of claim 2 wherein said second cover is attached to said container by a hinge member.

4. The system of claim 3 wherein said hinge member is a strip of a plastic material.

5. The system of claim 4 wherein said container is rectangular and has a depth between about 0.6 cm and 2.0 cm, a length between about 7.6 cm and 17.8 cm, and a width between about 2.5 cm and 12.7 cm.

6. The system of claim 5 wherein each of said depressions is rectangular and has a depth between about 0.025 centimeters (cm) and 0.55 cm, a length between about 1.0 cm and 2.4 cm, and a width between about 0.5 cm and 2.4 cm.

* * * * *